(12) United States Patent
Sams et al.

(10) Patent No.: US 9,023,870 B2
(45) Date of Patent: *May 5, 2015

(54) POSITIVE ALLOSTERIC MODULATORS OF NICOTINIC ACETYLCHOLINE RECEPTOR

(71) Applicant: H. Lundbeck A/S, Valby (DK)

(72) Inventors: Anette Graven Sams, Værløse (DK); Jørgen Eskildsen, København (DK); Ask Puschl, Frederiksberg (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,190

(22) Filed: Jun. 19, 2014

(65) Prior Publication Data

US 2014/0323523 A1    Oct. 30, 2014

Related U.S. Application Data

(63) Continuation of application No. 13/934,277, filed on Jul. 3, 2013, now Pat. No. 8,815,914, which is a continuation of application No. 13/542,687, filed on Jul. 6, 2012, now Pat. No. 8,598,213.

(51) Int. Cl.

| | |
|---|---|
| C07D 405/12 | (2006.01) |
| A61K 31/44 | (2006.01) |
| A61K 31/443 | (2006.01) |
| A61K 31/4433 | (2006.01) |
| A61K 31/4355 | (2006.01) |
| C07D 213/71 | (2006.01) |
| C07D 213/74 | (2006.01) |
| C07D 213/84 | (2006.01) |
| C07D 213/85 | (2006.01) |
| C07D 239/34 | (2006.01) |
| C07D 491/056 | (2006.01) |
| C07D 213/40 | (2006.01) |
| C07D 213/61 | (2006.01) |
| C07D 213/647 | (2006.01) |
| C07D 213/65 | (2006.01) |
| A61K 45/06 | (2006.01) |
| A61K 31/4427 | (2006.01) |
| A61K 31/436 | (2006.01) |
| A61K 31/505 | (2006.01) |

(52) U.S. Cl.
CPC .......... *A61K 31/4355* (2013.01); *C07D 213/71* (2013.01); *C07D 213/74* (2013.01); *C07D 213/84* (2013.01); *C07D 213/85* (2013.01); *C07D 239/34* (2013.01); *C07D 405/12* (2013.01); *C07D 491/056* (2013.01); *C07D 213/40* (2013.01); *C07D 213/61* (2013.01); *C07D 213/647* (2013.01); *C07D 213/65* (2013.01); *A61K 31/44* (2013.01); *A61K 31/443* (2013.01); *A61K 31/4433* (2013.01); *A61K 45/06* (2013.01); *A61K 31/4427* (2013.01); *A61K 31/436* (2013.01); *A61K 31/505* (2013.01)

(58) Field of Classification Search
None
See application file for complete search history.

(56) References Cited

U.S. PATENT DOCUMENTS

| | | | |
|---|---|---|---|
| 8,598,213 B2 | 12/2013 | Eskildsen et al. | |
| 8,815,914 B2 * | 8/2014 | Sams et al. | 514/336 |
| 2014/0010897 A1 | 1/2014 | Sams et al. | |
| 2014/0010898 A1 | 1/2014 | Eskildsen et al. | |
| 2014/0044806 A1 | 2/2014 | Eskildsen et al. | |

FOREIGN PATENT DOCUMENTS

| | | |
|---|---|---|
| WO | 2009/043784 A1 | 4/2009 |
| WO | 2010/137351 A1 | 12/2010 |
| WO | 2011/044195 A1 | 4/2011 |

OTHER PUBLICATIONS

International Search Report and Written Opinion issued Oct. 18, 2012 in International Application No. PCT/EP2012/063219 filed Jul. 6, 2012.

International Search Report and Written Opinion issued Sep. 24, 2013 in International Application No. PCT/EP2013/064088 filed Jul. 4, 2013.

Dinklo et al. 2011, "Characterication of 2-[[4-Fluoro-3-(trifluoromethyl)amino]-4-(4-pyridinyl)-5-thiazolemethanol (JNJ-1930942), a Novel Positive Allosteric Modulator of the α7 Nicotinic Acetylcholine Receptor" the Journal of Pharmacology and Experimental Therapeutics, vol. 336, No. 2, pp. 560-574.

Faghih et al., 2007, "Advances in the Discovery of Novel Positive Allosteric Modulators of the α7 Nicotinic Acetylcholine Receptor" Recent Patents of CNS Drug Discovery, 2, pp. 99-106.

Gundisch et al., 2011, "Nicotinic acetylcholine receptor liglands, a patent review (2006-2011)" Expert Opinion, Ther Patents, 21(12), pp. 1867-1896.

Hurst et al., 2005, "A Novel Positive Allosteric Modulator of the α7 Neuronal Nicotinic Acetylcholine Receptor in Vitro and In Vivo Characterization", The Journal of Neuroscience, 25(17), pp. 4396-4405.

Ng et al., 2007, "Nootropic α7 nicotinic receptor allosteric modulator derived from GABAA receptor modulators", PNAS, vol. 104, No. 19, pp. 8059-8064.

Timmermann et al., 2007, "An Allosteric Modulator of the α7 Nicotinic Acetylcholine Receptor Possessing Cognition-enhancing Properties in Vivo", The Journal of Pharmacology and Experimental Therapeutics, vol. 323, No., pp. 294-307.

International Search Report and Written Opinion issued Sep. 26, 2013 in International Application No. PCT/EP2013/064093 filed Jul. 4, 2013.

* cited by examiner

*Primary Examiner* — Zinna Northington Davis

(74) *Attorney, Agent, or Firm* — Mary Catherine Di Nunzio

(57) ABSTRACT

The present invention relates to compounds useful in therapy, to compositions comprising said compounds, and to methods of treating diseases comprising administration of said compounds. The compounds referred to are positive allosteric modulators (PAMs) of the nicotinic acetylcholine α7 receptor.

21 Claims, No Drawings

POSITIVE ALLOSTERIC MODULATORS OF NICOTINIC ACETYLCHOLINE RECEPTOR

CROSS-REFERENCE TO RELATED APPLICATIONS

This present application is a continuation of U.S. Application No. 13/934,277 filed Jul. 3, 2013 now U.S. Pat. No. 8,815,914, which is a continuation of U.S. application Ser. No. 13/542,687 filed Jul. 6, 2012 now U.S. Pat. No. 8,598,213. Each of these applications is hereby incorporated by reference in its entirety.

FIELD OF THE INVENTION

The present invention relates to compounds useful in therapy, to compositions comprising said compounds, and to methods of treating diseases comprising administration of said compounds. The compounds referred to are positive allosteric modulators (PAMs) of the nicotinic acetylcholine α7 receptor.

BACKGROUND OF THE INVENTION

Nicotinic acetylcholine receptors (nAChRs) belong to the super family of ligand gated ionic channels, and gate the flow of cations including calcium. The nAChRs are endogenously activated by acetylcholine (ACh) and can be divided into nicotinic receptors of the neuromuscular junction and neuronal nicotinic receptors (NNRs). The NNRs are widely expressed throughout the central nervous system (CNS) and the peripheral nervous system (PNS). The NNRs have been suggested to play an important role in CNS function by modulating the release of many neurotransmitters, for example, ACh, norepinephrine, dopamine, serotonin, and GABA, among others, resulting in a wide range of physiological effects.

Seventeen subunits of nAChRs have been reported to date, which are identified as α2-α10, β1-β4, γ, δ and ε. From these subunits, nine subunits, α2 through α7 and β2 through β4, prominently exist in the mammalian brain. Many functionally distinct nAChR complexes exist, for example five α7 subunits can form a receptor as a homomeric functional pentamer or combinations of different subunits can form heteromeric receptors such as α4β2 and α3β4 receptors (Gotti, C. et al., *Prog. Neurobiol.*, 2004, 74: 363-396;
Gotti, C. et al., *Biochemical Pharmacology*, 2009, 78: 703-711)

The homomeric α7 receptor is one of the most abundant NNRs, along with α4β2 receptors, in the brain, wherein it is heavily expressed in the hippocampus, cortex, thalamic nuclei, ventral tegmental area and substantia nigra (Broad, L. M. et al., *Drugs of the Future*, 2007, 32(2): 161-170, Poorthuis R B, *Biochem Pharmacol.* 2009, 1; 78(7):668-76).

The role of α7 NNR in neuronal signalling has been actively investigated. The α7 NNRs have been demonstrated to regulate interneuron excitability and modulate the release of excitatory as well as inhibitory neurotransmitters. In addition, α7 NNRs have been reported to be involved in neuroprotective effects in experimental models of cellular damage (Shimohama, S., *Biol Pharm Bull.* 2009, 32(3):332-6).

Studies have shown that α7 subunits, when expressed recombinant in-vitro, activate and desensitize rapidly, and exhibit relatively higher calcium permeability compared to other NNR combinations (Papke, R. L. et al., *J Pharmacol Exp Ther.* 2009, 329(2):791-807).

The NNRs, in general, are involved in various cognitive functions, such as learning, memory and attention, and therefore in CNS disorders, e.g. Alzheimer's disease (AD), Parkinson's disease (PD), attention deficit hyperactivity disorder (AHD), Tourette's syndrome, schizophrenia, bipolar disorder, pain and tobacco dependence (Keller, J. J. et al., *Behav. Brain Res.* 2005, 162: 143-52; Haydar, S. N. et al., *Curr Top Med Chem.* 2010; 10(2):144-52).

The α7 NNRs in particular, have also been linked to cognitive disorders including, for example, ADHD, autism spectrum disorders, AD, mild cognitive impairment (MCI), age associated memory impairment (AAMI) senile dementia, frontotemporal lobar degeneration. HIV associated dementia (HAD), HIV associated cognitive impairment (HIV-CI), Pick's disease, dementia associated with Lewy bodies, cognitive impairment associated with Multiple Sclerosis, Vascular Dementia, cognitive impairment in epilepsy, cognitive impairment associated with fragile X, cognitive impairment associated with Friedreich's Ataxia, and dementia associated with Down's syndrome, as well as cognitive impairment associated with schizophrenia. In addition, α7-NNRs have been shown to be involved in the neuroprotective effects of nicotine both in vitro (Jonnala, R. B. et al., *J. Neurosci. Res.*, 2001, 66: 565-572) and in vivo (Shimohama, S., *Brain Res.*, 1998, 779: 359-363) as well as in pain signalling. More particularly, neurodegeneration underlies several progressive CNS disorders, including, but not limited to, AD, PD, amyotrophic lateral sclerosis, Huntington's disease, dementia with Lewy bodies, as well as diminished CNS function resulting from traumatic brain injury. For example, the impaired function of α7 NNRs by beta-amyloid peptides linked to AD has been implicated as a key factor in development of the cognitive deficits associated with the disease (Liu, Q.-S., et al., *PNAS,* 2001, 98: 4734-4739). Thus, modulating the activity of α7 NNRs demonstrates promising potential to prevent or treat a variety of diseases indicated above, such as AD, other dementias, other neurodegenerative diseases, schizophrenia and neurodegeneration, with an underlying pathology that involves cognitive function including, for example, aspects of learning, memory, and attention (Thomsen. M. S. et al., *Curr Pharm Des.* 2010 January; 16(3):323-43; Olincy, A. et al., *Arch Gen Psychiatry.* 2006, 63(6):630-8; Deutsch, S. I., *Clin Neuropharmacol.* 2010, 33(3):114-20; Feuerbach, D., *Neuropharmacology.* 2009, 58(1): 254-63)

The NNR ligands, including α7 ligands, have also been implicated in weight control, diabetis inflammation, obsessive-compulsive disorder (OCD), angiogenesis and as potential analgesics (Marrero, M. B. et al., *J. Pharmacol. Exp. Ther.* 2010, 332(1):173-80; Vincler, M., *Exp. Opn. Invest. Drugs,* 2005, 14 (10): 1191-1198; Rosas-Ballina, M., *J. Intern Med.* 2009 265(6):663-79; Aries, H. R., *Int. J. Biochem. Cell Biol.* 2009, 41(7):1441-51; Tizabi, Y., *Biol Psychiatry.* 2002, 51(2): 164-71).

Nicotine is known to enhance attention and cognitive performance, reduced anxiety, enhanced sensory gating, and analgesia and neuroprotective effects when administered. Such effects are mediated by the non-selective effect of nicotine at multiple nicotinic receptor subtypes. However, nicotine also exerts adverse events, such as cardiovascular and gastrointestinal problems (Karaconji, I. B. et al., *Arh Hig Rada Toksikol.* 2005, 56(4):363-71). Consequently, there is a need to identify subtype-selective compounds that retain the beneficial effects of nicotine, or an NNR ligand, while eliminating or decreasing adverse effects.

Examples of reported NNR ligands are α7 NNR agonists, such as DMXB-A, SSR180711 and ABT-107, which have shown some beneficial effects on cognitive processing both in rodents and humans (see for example, Hajos, M., et al., *J. Pharmacol Exp Ther.* 2005, 312: 1213-22; Olincy, A. et al., *Arch Gen Psychiatry.* 2006 63(6):630-8; Pichat, P., et al., *Neuropsychopharmacology.* 2007 32(1):17-34; Bitner, R. S., *J Pharmacol Exp Ther.* 2010 1; 334(3):875-86). In addition, modulation of α7 NNRs have been reported to improve negative symptoms in patients with schizophrenia (Freedmen, R. et al., *Am J Psychiatry.* 2008 165(8):1040-7).

Despite the beneficial effects of NNR ligands, it remains uncertain whether chronic treatment with agonists affecting NNRs may provide suboptimal benefit due to sustained activation and desensitization of the NNRs, in particular the α7 NNR subtype. In contrast to agonists, administering a positive allosteric modulator (PAM) can reinforce endogenous cholinergic transmission without directly stimulating the target receptor. Nicotinic PAMs can selectively modulate the activity of ACh at NNRs, preserving the activation and deactivation kinetics of the receptor. Accordingly, α7 NNR-selective PAMs have emerged (Faghi, R., *Recent Pat CNS Drug Discov* 2007. 2(2):99-106).

Consequently, it would be beneficial to increase α7 NNR function by enhancing the effect of the endogenous neurotransmitter acetvicholine via PAMs. This could reinforce the endogenous cholinergic neurotransmission without directly activating α7 NNRs, like agonists. Indeed, PAMs for enhancing channel activity have been proven clinically successful for GABAa receptors where benzodiazepines and barbiturates, behave as PAMs acting at distinct sites (Hevers, W. et al., *Mol. Neurobiol.,* 1998, 18: 35-86).

To date, only a few NNR PAMs are known, such as 5-hydroxyindole (5-HI), ivermectin, galantamine, and SLURP-1, a peptide derived from acelylcholinesterase (AChE). Genistein, a kinase inhibitor was also reported to increase α7 responses. PNU-120596, a urea derivative, was reported to increase the potency ACh as well as improve auditory gating deficits induced by amphetamine in rats. Also, NS1738, JNJ-1930942 and compound 6 have been reported to potentiate the response of ACh and exert beneficial effect in experimental models of sensory and cognitive processing in rodents. Other NNR PAMs include derivatives of quinuclidine, indole, benzopyrazole, thiazole, and benzoisothiasoles (Hurst, R. S. et al., *J. Neurosci.* 2005, 25: 4396-4405; Faghih, R., *Recent Pat CNS Drug Discov.* 2007, 2(2):99-106; Timmermann, D. B., *J. Pharmacol. Exp. Ther.* 2007, 323(1):294-307; Ng, H. J. et al., *Proc. Natl. Acad. Sci. USA.* 2007, 8; 104(19):8059-64; Dinklo, T., *J. Pharmacol. Exp. Ther.* 2011, 336(2):560-74.).

WO 2009/043784 recites compounds of the overall structure

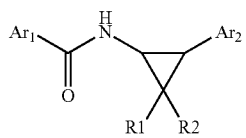

which compounds are said to be PAMs of the α7 NNR.

The α7 NNR PAMs presently known generally demonstrate weak activity, have a range of non-specific effects, or can only achieve limited access to the central nervous system where α7 NNRs are abundantly expressed. Accordingly, it would be beneficial to identify and provide new PAM compounds of α7 NNRs and compositions for treating diseases and disorders wherein α7 NNRs are involved. It would further be particularly beneficial if such compounds can provide improved efficacy of treatment while reducing adverse effects associated with compounds targeting neuronal nicotinic receptors by selectively modulating α7 NNRs.

WO 2010/137351 recites compounds of the overall structure

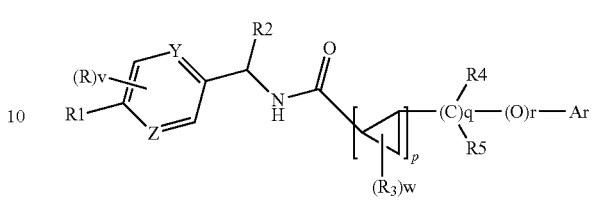

as calcium or sodium channel blockers i.e. compounds related to a pharmacological mechanism distinguished from the compounds of the present invention.

SUMMARY OF THE INVENTION

The objective of the present invention is to provide compounds that are positive allosteric modulators (PAMs) of the nicotinic acetylcholine receptor subtype α7.

The compounds of the present invention are defined by formula [I] below:

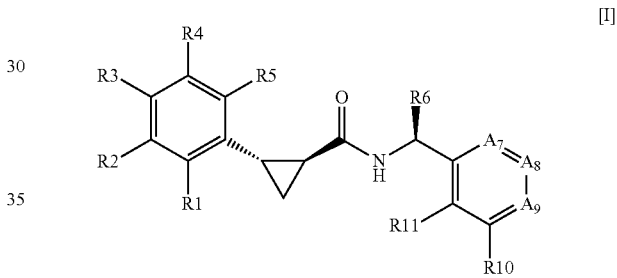

wherein R1, R2, R3, R4 and R5 are H;
R6 is selected from methyl and hydroxymethyl;
A7 is C—R7. A8 is N and A9 is C—R9;
R7, R10 and R11 are H;
R9 is OR12, wherein R12 represents a monocyclic saturated ring moiety having 46 ring atoms wherein one of said ring atoms is O and the rest is C;
and pharmaceutically acceptable salts thereof.

In one embodiment, the invention relates to a compound according to formula [I], and pharmaceutically acceptable salts thereof, for use as a medicament.

In one embodiment, the invention relates to a compound according to formula [I], and pharmaceutically acceptable salts thereof, for use in the treatment of a disease or disorder selected from psychosis; schizophrenia; cognitive disorders; cognitive impairment associated with schizophrenia; attention deficit hyperactivity disorder (ADHD); autism spectrum disorders. Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

In one embodiment, the invention relates to a pharmaceutical composition comprising a compound according to formula [I] and pharmaceutically acceptable salts thereof, and one or more pharmaceutically acceptable carrier or excipient.

In one embodiment, the invention relates to a kit comprising a compound according to formula [I], and pharmaceutically acceptable salts thereof, together with a compound selected from the list consisting of acetylcholinesterase inhibitors; glutamate receptor antagonists; dopamine transport inhibitors; noradrenalin transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

In one embodiment, the invention relates to a method for the treatment of a disease or disorder selected from psychosis; schizophrenia; cognitive disorders; cognitive impairment associated with schizophrenia; attention deficit hyperactivity disorder (ADHD); autism spectrum disorders, Alzheimer's disease (AD); mild cognitive impairment (MCI); age associated memory impairment (AAMI); senile dementia; AIDS dementia Pick's disease; dementia associated with Lewy bodies; dementia associated with Down's syndrome; Huntington's disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain, which method comprises the administration of a therapeutically effective amount of a compound according to formula [I], and pharmaceutically acceptable salts thereof.

In one embodiment, the invention relates to the use of a compound according to formula [I], and pharmaceutically acceptable salts thereof, for the manufacture of a medicament for the treatment of a disease or disorder selected from psychosis; schizophrenia; cognitive disorders; cognitive impairment associated with schizophrenia; attention deficit hyperactivity disorder (ADHD); autism spectrum disorders, Alzheimers disease (AD); mild cognitive impairment (MCI); age associated memory impairment (AAMI); senile dementia; AIDS dementia; Pick's disease; dementia associated with Lewy bodies; dementia associated with Down's syndrome; Huntington's disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

Definitions

In the present context. "alkyl" is intended to indicate a straight, branched and/or cyclic saturated hydrocarbon. In particular "$C_{1-6}$alkyl" is intended to indicate such hydrocarbon having 1, 2, 3, 4, 5 or 6 carbon atoms. Examples of $C_{1-6}$alkyl include methyl, ethyl, propyl, butyl, pentyl, hexyl, cyclopropyl, cyclobutyl, cyclopentyl, cyclohexyl, methylcyclopropyl, 2-methylpropyl and tert-butyl. Examples of substituted $C_{1-6}$alkyl include e.g. fluoromethyl and hydroxymethyl.

In the present context, "hydroxy" is intended to indicate —OH.

In the present context, a "monocyclic moiety" is intended to cyclic moiety comprising only one ring, said cyclic moiety can be saturated or unsaturated.

In the present context, "ring atom" is intended to indicate the atoms constituting a ring, and ring atoms are selected from C, N, O and S. As an example, benzene and toluene both have 6 carbons as ring atoms whereas pyridine has 5 carbons and 1 nitrogen as ring atoms.

In the present context, "enantiomeric excess" represents the % excess of a compound in a mixture of compound enantiomers. If for example an enantiomeric excess is 90% then the ratio of the compound to its enantiomer is 95:5 and if an enantiomeric excess is 95% then the ratio of the compound to its enantiomer is 97.5:2.5. Likewise, "diastereomeric excess" represents % excess of a compound in a mixture of compound diastereomers.

In the present context, pharmaceutically acceptable salts include pharmaceutically acceptable acid addition salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in Berge, S. M. et al., *J. Pharm. Sci* 1977, 66, 2, which is incorporated herein by reference.

In the present context, pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier may include any sustained release material known in the art, such as glyceryl monostearate or glyceryl distearate, alone or mixed with a wax.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. In one aspect of the present invention, "treatment" and "treating" refers to prophylactic (preventive) treatment. In another aspect. "treatment" and "treating" refers to (curative) treatment. The patient to be treated is preferably a mammal, in particular a human being.

In the present context, the term "cognitive disorders" is intended to indicate disorders characterized by abnormalities in aspects of perception, problem solving, language, learning, working memory, memory, social recognition, attention and pre-attentional processing, such as by not limited to Attention Deficit Hyperactivity Disorder (ADHD), autism spectrum disorders, Alzheimer's disease (AD), mild cognitive impairment (MCI), age associated memory impairment (AAMI), senile dementia, vascular dementia, frontotemporal lobe dementia, Pick's disease, dementia associated with Lewy bodies, and dementia associated with Down's syndrome, cognitive impairment associated with Multiple Sclerosis, cognitive impairment in epilepsy, cognitive impairment associated with fragile X, cognitive impairment associated with neurofibromatosis, cognitive impairment associated with Friedreich's Ataxia, progressive supranuclear palsy (PSP), HIV associated dementia (HAD), HIV associated cognitive impairment (HIV-CI), Huntington's Disease, Parkinson's disease (PD), obsessive-compulsive disorder (OCD), traumatic brain injury, epilepsy, post-traumatic stress, Wernicke-Korsakoff syndrome (WKS), post-traumatic amnesia, cognitive deficits associated with depression as well as cognitive impairment associated with schizophrenia.

The cognitive enhancing properties of a compound can be assessed e.g. by the attentional set-shifting paradigm which is an animal model allowing assessment of executive functioning via intra-dimensional (ID) versus extra-dimensional (ED) shift discrimination learning. The study can be performed by testing whether the compound is attenuating "attentional performance impairment" induced by subchronic PCP administration in rats as described by Rodefer, J. S. et al., *Eur. J. Neurosci.* 2005, 21:1070-1076.

In the present context, the term "autism spectrum disorders" is intended to indicate disorders characterized by widespread abnormalities of social interactions and verbal and non-verbal communication, as well as restricted interests, repetitive behavior and attention, such as by not limited to autism, Asperger syndrome, Pervasive Developmental Disorder Not Otherwise Specified (PDD-NOS), Rett syndrome. Angelmann syndrome, fragile X, DiGeorge syndrome and Childhood Disintegrative Disorder.

In the present context, the term "inflammatory disorders" is intended to indicate disorders characterized by abnormalities in the immune system such as by not limited to, allergic reactions and myopathies resulting in abnormal inflammation as well as non-immune diseases with etiological origins in inflammatory processes are thought to include by not be limited to cancer, atherosclerosis, osteoarthritis, rheumatoid arthritis and ischaemic heart disease.

DETAILED DESCRIPTION OF THE INVENTION

The present inventors have found that certain new compounds are positive allosteric modulators (PAMs) of NNRs, and as such may be used in the treatment of various disorders.

PAMs of NNRs may be dosed in combination with other drugs in order to achieve more efficacious treatment in certain patient populations. An α7 NNR PAM may act synergistically with another drug, this has been described in animals for the combination of compounds affecting nicotinic receptors, including α7 NNRs and 02 antagonism (Wiker. C., *Int. J. Neuropsychopharmacol.* 2008, 11(6):845-50).

Thus, compounds of the present invention may be useful treatment in the combination with another drug e.g. selected from acetylcholinesterase inhibitors, glutamate receptor antagonists, dopamine transport inhibitors, noradrenalin transport inhibitors, D2 antagonists, D2 partial agonists, PDE10 antagonists, 5-HT2A antagonists, 5-HT6 antagonists and KCNQ antagonists, lithium, sodium channel blockers, GABA signalling enhancers.

In one embodiment, compounds of the present invention are used for treatment of patients who are already in treatment with another drug selected from the list above. In one embodiment, compounds of the present invention are adapted for administration simultaneous with said other drug. In one embodiment compounds of the present invention are adapted for administration sequentially with said other drug. In one embodiment, compounds of the present invention are used as the sole medicament in treatment of a patient. In one embodiment, compounds of the present invention are used for treatment of patients who are not already in treatment with another drug selected from the list above.

Embodiments According To The Invention

In the following, embodiments of the invention are disclosed. The first embodiment is denoted E1, the second embodiment is denoted E2 and so forth.

E1. A compound according to formula [I]

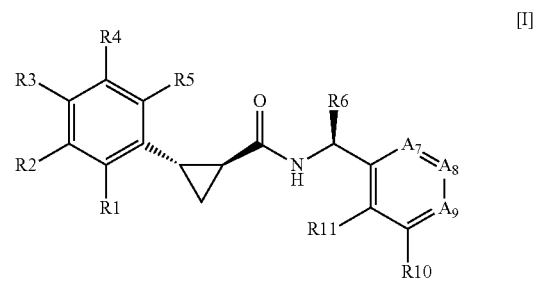

wherein R1, R2, R3, R4 and R5 are H;
R6 is selected from methyl and hydroxymethyl;
A7 is C—R7, A8 is N and A9 is C—R9;
R7, R10 and R11 are H;
R9 is OR12, wherein R12 represents a monocyclic saturated ring moiety having 4-6 ring atoms wherein one of said ring atoms is O and the rest is C;
and pharmaceutically acceptable salts thereof.

E2. The compound according to embodiment 1, wherein R6 is methyl.

E3. The compound according to embodiment 1, wherein R6 is hydroxymethyl.

E4. The compound according to any of embodiments 1-3 having a diastereomeric excess of at least 80% such as at least 85%, such as at least 90%, such as at least 95%.

E5. The compound according to embodiment 1 selected from
13: (1S,2S)-2-Phenyl-cyclopropanecarboxylic acid ((S)-1-{6-[(S)-(tetrahydro-furan-3-yl)oxy]-pyridin-3-yl}-ethyl)-amide;
14: (1S,2S)-2-Phenyl-cyclopropanecarboxylic acid ((S)-1-{6-[(R)-(tetrahydro-furan-3-yl)oxy]-pyridin-3-yl}-ethyl)-amide;
19: (1S,2S)-2-Phenyl-cyclopropanecarboxylic acid {(S)-1-[6-(oxetan-3-yloxy)-pyridin-3-yl]-ethyl}-amide;

43: (1S,2S)-2-Phenyl-cyclopropanecarboxylic acid ((R)-2-hydroxy-1-{6-[(R)-(tetrahydro-furan-3-yl)oxy]-pyridin-3-yl}-ethyl)-amide;
44: (1S,2S)—N-[(1R)-2-hydroxy-1-[6-[(3S)-tetrahydrofuran-3-yl]oxy-3-pyridyl]ethyl]-2-phenyl-cyclopropanecarboxamide;
45: (1S,2S)-2-Phenyl-cyclopropanecarboxylic acid {(R)-2-hydroxy-1-[6-(tetrahydro-pyran-4-yloxy)-pyridin-3-yl]-ethyl}-amide;
and pharmaceutically acceptable salts of any of these compounds.

E6. The compound according to embodiment 1, which is
13: (1S,2S)-2-Phenyl-cyclopropanecarboxylic acid ((S)-1-{6-[(S)-(tetrahydro-furan-3-yl)oxy]-pyridin-3-yl}-ethyl)-amide;
and pharmaceutically acceptable salts thereof.

E7. The compound according to embodiment 1, which is
14: (1S,2S)-2-Phenyl-cyclopropanecarboxylic acid ((S)-1-{6-[(R)-(tetrahydro-furan-3-yl)oxy]-pyridin-3-yl}-ethyl)-amide;
and pharmaceutically acceptable salts thereof.

E8. The compound according to embodiment 1, which is
19: (1S,2S)-2-Phenyl-cyclopropanecarboxylic acid {(S)-1-[6-(oxetan-3-yloxy)-pyridin-3-yl]-ethyl}-amide;
and pharmaceutically acceptable salts thereof.

E9. The compound according to embodiment 1, which is
43: (1S,2S)-2-Phenyl-cyclopropanecarboxylic acid ((R)-2-hydroxy-1-{6-[(R)-(tetrahydro-furan-3-yl)oxy]-pyridin-3-yl}-ethyl)-amide;
and pharmaceutically acceptable salts thereof.

E10. The compound according to embodiment 1, which is
44: (1S,2S)—N-[(1R)-2-hydroxy-1-[6-[(3S)-tetrahydrofuran-3-yl]oxy-3-pyridyl]ethyl]-2-phenyl-cyclopropanecarboxamide;
and pharmaceutically acceptable salts thereof.

E11. The compound according to embodiment 1, which is
45: (1S,2S)-2-Phenyl-cyclopropanecarboxylic acid {(R)-2-hydroxy-1-[6-(tetrahydro-pyran-4-yloxy)-pyridin-3-yl]-ethyl}-amide;
and pharmaceutically acceptable salts thereof.

E12. A compound according to any of embodiments 1-11, for use as a medicament.

E13. A compound according to any of embodiments 1-11, for use in therapy.

E14. A compound according to any of embodiments 1-11, for use in the treatment of a disease or disorder selected from psychosis; schizophrenia; cognitive disorders; cognitive impairment associated with schizophrenia; attention deficit hyperactivity disorder (ADHD); autism spectrum disorders. Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

E15. The compound according to embodiment 14, wherein said a disease or disorder is selected from schizophrenia; AD; ADHD; autism spectrum disorders; PD; amyotrophic lateral sclerosis; Huntington's disease; dementia associated with Lewy bodies and pain.

E16. The compound according to embodiment 15, wherein said disease or disorder is selected from schizophrenia; AD; ADHD and autism spectrum disorders.

E17. The compound according to embodiment 16, wherein said disease or disorder is selected from negative and/or cognitive symptoms of schizophrenia.

E18. The compound according to any of embodiments 1-11, for use concomitantly or sequentially with a therapeutically effective amount of a compound selected from the list consisting of acetylcholinesterase inhibitors; glutamate receptor antagonists; dopamine transport inhibitors; noradrenalin transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers in the treatment of a disease or disorder according to any of embodiments 14-17.

E19. A pharmaceutical composition comprising a compound according to any of embodiments 1-11, and one or more pharmaceutically acceptable carrier or excipient.

E20. The composition according to embodiment 19, which composition additionally comprises a second compound selected from the list consisting of acetylcholinesterase inhibitors; glutamate receptor antagonists; dopamine transport inhibitors; noradrenalin transport inhibitors; D2 antagonists; D2 partial agonists; PDE10 antagonists; 5-HTZA antagonists; 5-HT6 antagonists; KCNQ antagonists; lithium; sodium channel blockers and GABA signaling enhancers.

E21. The composition according to embodiment 20, wherein said second compound is an acetylcholinesterase inhibitor.

E22. A kit comprising a compound according to any of embodiments 1-11, together with a second compound selected from the list consisting of acetylcholinesterase inhibitors; glutamate receptor antagonists; dopamine transport inhibitors; noradrenalin transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

E23. The kit according to embodiment 22, wherein said second compound is an acetylcholinesterase inhibitor.

E24. A method for the treatment of a disease or disorder selected from psychosis; schizophrenia; cognitive disorders; cognitive impairment associated with schizophrenia; attention deficit hyperactivity disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain, which method comprises the administration of a therapeutically effective amount of a compound according to any of embodiments 1-11 to a patient in need thereof.

E25. The method according to embodiment 24, wherein said disease or disorder is selected from schizophrenia; AD; ADHD; autism spectrum disorders; PD; amyotrophic lateral sclerosis; Huntington's disease; dementia associated with Lewy bodies and pain.

E26. The method according to embodiment 25, wherein said disease or disorder is selected from schizophrenia; AD; ADHD and autism spectrum disorders.

E27. The method according to embodiment 26, wherein said treatment comprises the treatment of negative and/or cognitive symptoms of schizophrenia.

E28. The method according to any of embodiments 24-27, wherein said treatment further comprises the administration of a therapeutically effective amount of a second compound selected from the list consisting of acetylcholinesterase inhibitors; glutamate receptor antagonists; dopamine transport inhibitors; noradrenalin transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

E29. The method according to embodiment 28, wherein said second compound is an acetylcholinesterase inhibitor.

E30. Use of a compound according to any of embodiments 1-11, for the manufacture of a medicament for the treatment of a disease or disorder selected from psychosis; schizophrenia; cognitive disorders; cognitive impairment associated with schizophrenia; attention deficit hyperactivity disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

E31. The use according to embodiment 30, wherein said disease or disorder is selected from schizophrenia; AD; ADHD; autism spectrum disorders; PD; amyotrophic lateral sclerosis; Huntington's disease; dementia associated with Lewy bodies and pain.

E32. The use according to embodiment 31, wherein said disease or disorder is selected from schizophrenia; AD; ADHD and autism spectrum disorders.

E33. The use according to embodiment 32, wherein said disease is the positive, negative and/or cognitive symptoms of schizophrenia.

E34. The use according to any of embodiments 30-33, wherein said manufacture further comprises the use of a second compound selected from the list consisting of acetylcholinesterase inhibitors; glutamate receptor antagonists; dopamine transport inhibitors; noradrenalin transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

E35. The use according to embodiment 34, wherein said second compound is an acetylcholinesterase inhibitor.

The compounds of the invention may exist in unsolvated as well as in solvated forms in which the solvent molecules are selected from pharmaceutically acceptable solvents such as water, ethanol and the like. In general, such solvated forms are considered equivalent to the unsolvated forms for the purposes of this invention.

The compounds of the present invention have three asymmetric centers with fixed stereochemistry indicated by the arrows below.

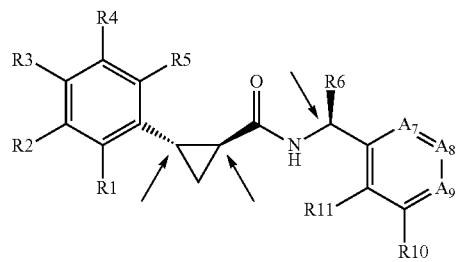

The compounds of the present invention are manufactured from two chiral intermediates with one and two asymmetric centers, respectively, as illustrated by the examples below.

In this context is understood that when specifying the enantiomeric form of the intermediate, then the intermediate is in enantiomeric excess, e.g. essentially in a pure, mono-enantiomeric form. Accordingly, the resulting compounds of the invention are having a diastereomeric excess of at least 80%. One embodiment of the invention relates to a compound of the invention having a diastereomeric excess of at least 80% such as at least 85%, such as at least 90%, preferably at least 95% or at least 97% with reference to the three assymetric centers indicated above.

Dependent on the substituent R9, the compounds of the present invention may furthermore have one or more additional asymmetric centers. It is intended that any optical isomers (i.e. enantiomers or diastereomers), in the form of separated, pure or partially purified optical isomers and any mixtures thereof including racemic mixtures, i.e. a mixture of stereoisomers, which have emerged because of asymmetric centers in substituent R9, are included within the scope of the invention.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers. Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include suppositories, sprays, ointments, cremes, gels, inhalants, dermal patches, implants, etc.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and Intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

EXAMPLES

The invention will be illustrated by the following non-limiting examples.

Methods of Preparation of the Compounds of the Invention. Compounds according to the present invention can be prepared as described in WO 2013/007621. For convenience, the number indicated in bold in front of the exemplified compound name refers to the corresponding compound number in WO 2013/007621. Exemplified compounds of the present invention are listed in Table 1 below.

TABLE 1

| Compound Name | | Formula |
|---|---|---|
| 13 | (1S,2S)-2-Phenyl-cyclopropanecarboxylic acid ((S)-1-{6-[(S)-(tetrahydro-furan-3-yl)oxy]-pyridin-3-yl}-ethyl)-amide | |
| 14 | (1S,2S)-2-Phenyl-cyclopropanecarboxylic acid ((S)-1-{6-[(R)-(tetrahydro-furan-3-yl)oxy]-pyridin-3-yl}-ethyl)-amide | |
| 19 | (1S,2S)-2-Phenyl-cyclopropanecarboxylic acid {(S)-1-[6-(oxetan-3-yloxy)-pyridin-3-yl]-ethyl}-amide | |
| 43 | (1S,2S)-2-Phenyl-cyclopropanecarboxylic acid ((R)-2-hydroxy-1-{6-[(R)-(tetrahydro-furan-3-yl)oxy]-pyridin-3-yl}-ethyl)-amide | |
| 44 | (1S,2S)-N-[(1R)-2-hydroxy-1-[6-[(3S)-tetrahydrofuran-3-yl]oxy-3-pyridyl]ethyl]-2-phenyl-cyclopropanecarboxamide | |
| 45 | (1S,2S)-2-Phenyl-cyclopropanecarboxylic acid {(R)-2-hydroxy-1-[6-(tetrahydro-pyran-4-yloxy)-pyridin-3-yl]-ethyl}-amide | |

In Vitro Assays

The nicotinic acetylcholine receptor α7 is a calcium-permeable ion channel, whose activity can be measured by over expression in mammalian cells or oocytes. These two individual assays are described in Example 1 and 2, respectively.

ABBREVIATIONS

DMEM/F12=Dulbecco's Modified Eagle Medium, F12=Nutrient mix, FBS=Fetal Bovine Serum. Pen=Penicillin. Strep=streptomycin, G-418=Geneticin, HBSS=Hanks Balanced Salt Solution. HEPES=(4-(2-hydroxyethyl)-1-piperazineethanesulfonic acid), FDSS7000=Functional Drug Screening System from Hamamatso, OR2 buffer=Oocyte Ringer.

EXAMPLE 1

α7 NNR Flux Assay

The nicotinic acetylcholine receptor α7 is a calcium-permeable ion channel, whose activity can be measured by over expression in mammalian cells or oocytes. In this version of the assay, the human α7 receptor is stably expressed in the rat GH4C1 cell line. The assay was used to identify positive allosteric modulators (PAMs) of the α7 receptor. Activation of the channel was measured by loading cells with the calcium-sensitive fluorescent dye Calcium-4 (Assay kit from Molecular Devices), and then measuring real-time changes in fluorescence upon treatment with test compounds.

The cell line ChanClone GH4C1-nAChRalpha7 from Genionics was seeded from frozen stock in 384-well plates in culture media 2-3 days before experiment to form an approximately 80% confluent layer on the day of experiment.

Cell Plating and Dye Loading

The cell culture were split into "22.5 cm×22.5 cm"-plates with approximately 100×10$^3$ cells/cm$^2$. After four days incubation in a humidified incubator at 37° C. and 5% $CO_2$, it had grown to an 80-90% confluent layer, and the cells were harvested.

Culture Media:
 500 mL DMEM/F12 (Gibco 31331)
 50 mL FBS (Gibco 10091-155, lot 453269FD)
 5 mL Sodium Pyruvate (Gibco 11360)
 5 mL Pen/Strep (Gibco 15140)
 0.1 mg/mL G-418 (Gibco 11811-064)

Two or three days before the experiment the cells were seeded in 384 well plates from Greiner bio-one (781946. CELLCOAT, Poly-D-Lysine, black, µClear).

The media was poured off and the plate washed with PBS and left to drain. 5 mL Trypsin was added, cells were washed and incubated (at room temperature) for about 10 seconds. Trypsin was poured of quickly and the cells were incubated for 2 minutes at 37° C. (if the cells were not already detached). Cells were resuspended in 10 mL culture media and transferred to 50 mL tubes.

The cell suspension was counted (NucleoCounter, total cell count) from the first plates to estimate the total cell number of the whole batch.

The cells were seeded in 384 well plates with 30 µL/well (30000 cells/well) while stirring the cell suspension or otherwise preventing the cells from precipitating.

The plates were incubated at room temperature for 30-45 minutes.

The plates were placed in incubator for two days (37° C. and 5% $CO_2$).

Loading the Cells

The loading buffer was 5% v/v Calcium-4 Kit and 2.5 mM Probenecid in assay buffer.
 190 mL assay buffer (HBSS with 20 mM Hepes, pH 7.4 and 3 mM $CaCl_2$)
 10 mL Kit-solution (Calcium 4 assay kit component A)
 2 mL 250 mM Probenecid This volume was enough for 3×8 cell plates.

Culture media were removed from the cell plates and 20 µL loading buffer was added in each well. The cell plates were placed in trays and incubated 90 minutes in the incubator (37° C.). Thereafter the plates were incubated 30 minutes at room temperature. The plates were protected from light during the entire incubation time.

Now the cell plates were ready to run in the Functional Drug Screening System (FDSS).

The assay buffer was HBSS with 20 mM HEPES, pH 7.4 and 3 mM $CaCl_2$.

FDSS Ca Assay 200 nL 10 mM compound solution in DMSO was diluted in 50 µL assay buffer. The final test concentrations in the cell plates were 20-10-5-2.5-1.25-0.625-0.312-0.156-0.078-0.039 µM. Assay buffer and 3 µM PNU-120596 (Hurst et al., Neurosci. 2005, 25 (17): 4396-405) were used for control.

The agonist acetylcholine was added to a final concentration of 20 µM (~EC100). In the FDSS7000 the Ex480-Em540 was measured with 1 second intervals. The baseline was made of 5 frames before addition of test compounds, and 95 frames more were made before addition of acetylcholine. The measurement stopped 30 frames after the $2^{nd}$ addition. Raw data for each well were collected as "the maximum fluorescence count" in the interval 100-131 seconds and as "the average fluorescence count" in the Interval 96-100 seconds. The positive allosteric modulation in the $2^{nd}$ addition was the enhancement of agonist response with test compound compared to agonist alone.

Results were calculated as % modulation of test compound compared to the reference PNU-120596 set to 100%. From these data $EC_{50}$ curves were generated giving $EC_{50}$, hill and maximum stimulation.

The compounds of the invention were shown to be PAMs of the α7 receptor. The compounds of the present invention characterized in the flux assay generally possess $EC_{50}$ values below 20.000 nM or less such as below 10.000 nM. Many compounds, in fact have $EC_{50}$ values below 5.000 nM. Table 2 shows $EC_{50}$ values for exemplified compounds of the invention.

TABLE 2

| Compound | $EC_{50}$ (nM) |
|---|---|
| 13 | 1600 |
| 14 | 1600 |
| 19 | 2400 |
| 43 | 2900 |
| 44 | 4600 |
| 45 | 2900 |

EXAMPLE 2

α7NNR Oocyte Assay

Expression of α7 nACh Receptors in *Xenopus* Oocytes.

Oocytes are surgically removed from mature female *Xenepus laevis* anaesthetized in 0.4% MS-222 for 10-15 min. The oocytes are then digested at room temperature for 2-3 hours with 0.5 mg/mL collagenase (type IA Sigma-Aldrich) In OR2 buffer (82.5 mM NaCl, 2.0 mM KCl, 1.0 mM $MgCl_2$ and 5.0 mM HEPES, pH 7.6). Oocytes avoid of the follicle layer are selected and incubated for 24 hours in Modified Barth's Saline buffer (88 mM NaCl, 1 mM KCl, 15 mM HEPES, 2.4 mM $NaHCO_3$, 0.41 mM $CaCl_2$, 0.82 mM $MgSO_4$, 0.3 mM $Ca(NO_3)_2$) supplemented with 2 mM sodium pyruvate, 0.1 U/l penicillin and 0.1 µg/l streptomycin. Stage IV oocytes are identified and injected with 4.2-48 nl of nuclease free water containing 0.1-1.2 ng of cRNA coding for human α7 nACh receptors or 3.0-32 ng of cRNA coding for rat α7 nACh receptors and incubated at 18° C. for 1-10 days when they are used for electrophysiological recordings.

Electrophysiological Recordings of α7 nACh Receptors Expressed in Oocyte.

Oocytes are used for electrophysiological recordings 1-10 days after injection. Oocytes are placed in a 1 mL both and perfused with Ringer buffer (115 mM NaCl, 2.5 mM KCl, 10 mM HEPES, 1.8 mM $CaCl_2$, 0.1 mM $MgCl_2$, pH 7.5). Cells are impaled with agar plugged 0.2-1 MΩ electrodes containing 3 M KCl and voltage clamped at −90 mV by a GeneClamp 500B amplifier. The experiments are performed at room temperature. Oocytes are continuously perfused with Ringer buffer and the drugs are applied in the perfusate. ACh (30 µM) applied for 30 sec are used as the standard agonist for activation of the α7 nACh receptors. In the standard screening set-up the new test compound (10 µM or 30 µM) are applied for 1 min of pre-application allowing for evaluation of agonistic activity followed by 30 sec of co-application with ACh (30 µM) allowing for evaluation of PAM activity. The response of co-application was compared to the agonistic response obtained with ACh alone. The drug induced effects on both the peak response and the total charge (AUC) response are calculated thus giving the effect of drug induced PAM activity as fold modulation of the control response.

For more elaborate studies doses-response curves can be performed for evaluation of max-fold modulation and $EC_{50}$ values for both peak and AUC responses.

The invention claimed is:

1. A method of treating a subject suffering from schizophrenia comprising administering a therapeutically effective amount of a compound according to formula [I]

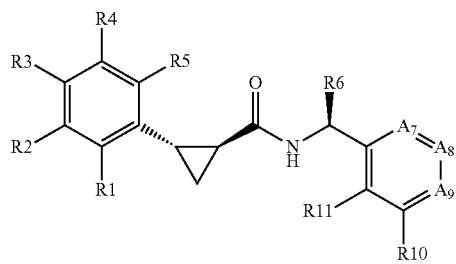

wherein R1, R2, R3, R4 and R5 are H;
R6 is selected from methyl and hydroxymethyl;
A7 is C-R7, A8 is N and A9 is C-R9;
R7, 10 and R11 are H; and
R9 is OR12, wherein R12 represents a monocyclic saturated ring moiety having 4-6 ring atoms wherein one of said ring atoms is O and the rest is C;
or a pharmaceutically acceptable salt thereof.

2. The method of claim 1, wherein the compound is (1S, 2S)-2-Phenyl-cyclopropanecarboxylic acid ((S)-1-{6-[(S)-(tetrahydro-furan-3-yl)oxy]-pyridin-3-yl}-ethyl)-amide or a pharmaceutically acceptable salt thereof.

3. The method of claim 1, wherein the compound (1S,2S)-2-Phenyl-cyclopropanecarboxylic acid ((S)-1-{6-[(R)-(tetrahydro-furan-3-yl)oxy]-pyridin-3-yl}-ethyl)-amide or a pharmaceutically acceptable salt thereof.

4. The method of claim 1, wherein the compound is (1S, 2S)-2-Phenyl-cyclopropanecarboxylic acid {(S)-1-[6-(oxetan-3-yloxy)-pyridin-3-yl]-ethyl}-amide or a pharmaceutically acceptable salt thereof.

5. The method of claim 1, wherein the compound is (1S, 2S)-2-Phenyl-cyclopropanecarboxylic acid ((R)-2-hydroxy-1-{6-[(R)-(tetrahydro-furan-3-yl)oxy]-pyridin-3-yl}-ethyl)-amide or a pharmaceutically acceptable salt thereof.

6. The method of claim 1, wherein the compound is (1S, 2S)-N-[(1R)-2-hydroxy-1 -[6-[(3S)-tetrahydro-furan-3-yl]oxy-3-pyridyl]ethyl]-2-phenyl-cyclopropanecarboxamide or a pharmaceutically acceptable salt thereof.

7. The method of claim 1, wherein the compound is (1S, 2S)-2-Phenyl-cyclopropanecarboxylic acid {(R)-2-hydroxy-1-[6-(tetrahydro-pyran-4-yloxy)-pyridin-3-yl]-ethyl}-amide or a pharmaceutically acceptable salt thereof.

8. A method of treating a subject suffering from cognitive impairment comprising administering a therapeutically effective amount of a compound according to formula [I]

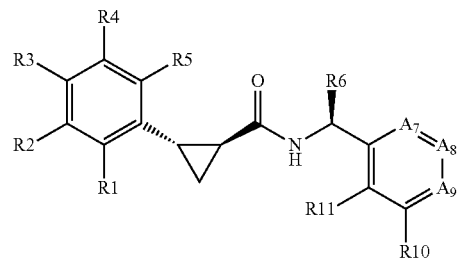

wherein R1, R2, R3, 4 and R5 are H;
R6 is selected from methyl and hydroxymethyl;
A7 is C-R7, A8 is N and A9 is C-R9;
R7, R10 and R11 are H; and
R9 is OR12, wherein R12 represents a monocyclic saturated ring moiety having 4-6 ring atoms wherein one of said ring atoms is O and the rest is C;
or a pharmaceutically acceptable salt thereof.

9. The method of claim 8, wherein the compound is (1S, 2S)-2-Phenyl-cyclopropanecarboxylic acid ((S)-1-{6-[(S)-(tetrahydro-furan-3-yl)oxy]-pyridin-3-yl}-ethyl)-amide or a pharmaceutically acceptable salt thereof.

10. The method of claim 8, wherein the compound (1S, 2S)-2-Phenyl-cyclopropanecarboxylic acid ((S)-1-{6-[(R)-(tetrahydro-furan-3-yl)oxy]-pyridin-3-yl}ethyl)-amide or a pharmaceutically acceptable salt thereof.

11. The method of claim 8, wherein the compound is (1S, 2S)-2-Phenyl-cyclopropanecarboxylic acid (S)-1-[6-(oxetan-3-yloxy)-pyridin-3-yl]-ethyl)-amide or a pharmaceutically acceptable salt thereof.

12. The method of claim 8, wherein the compound is (1S, 2S)-2-Phenyl-cyclopropanecarboxylic acid ((R)-2-hydroxy-1-{6-[(R)-(tetrahydro-furan-3-yl)oxy]-pyridin-3-yl}-ethyl)-amide or a pharmaceutically acceptable salt thereof.

13. The method of claim 8, wherein the compound is (1S, 2S)-N-[(1R)-2-hydroxy-1-[6-[(3S)-tetrahydrofuran-3-yl]oxy-3-pyridyl]ethyl]-2-phenyl-cyclopropanecarboxamide or a pharmaceutically acceptable salt thereof.

14. The method of claim 8, wherein the compound is (1S, 2S)-2-Phenyl-cyclopropanecarboxylic acid {(R)-2-hydroxy-1-[6-(tetrahydro-pyran-4-yloxy)-pyridin-3-yl]-ethyl}-amide or a pharmaceutically acceptable salt thereof.

15. A method of treating a subject suffering from pain comprising administering a therapeutically effective amount of a compound according to formula [I]

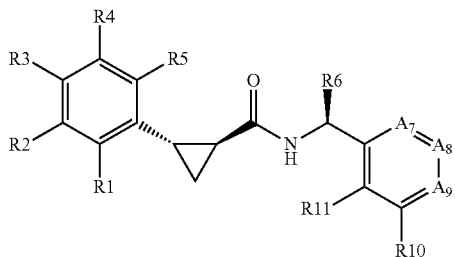

wherein R1, 2, 3, 4 and R5 are H;
R6 is selected from methyl and hydroxymethyl;
A7 is C-R7, A8 is N and A9 is C-R9;
R7, 10 and R11 are H; and
R9 is OR12, wherein R12 represents a monocyclic saturated ring moiety having 4-6 ring atoms wherein one of said ring atoms is O and the rest is C;
or a pharmaceutically acceptable salt thereof.

16. The method of claim 15, wherein the compound is (1S,2S)-2-Phenyl-cyclopropanecarboxylic acid ((S)-1-{6-[(S)-(tetrahydro-furan-3-yl)oxy]-pyridin-3-yl}-ethyl)-amide or a pharmaceutically acceptable salt thereof.

17. The method of claim 15, wherein the compound (1S, 2S)-2-Phenyl-cyclopropanecarboxylic acid ((S)-1-{6-[(R)-(tetrahydro-furan-3-yl)oxy]-pyridin-3-yl}-ethyl)-amide or a pharmaceutically acceptable salt thereof.

18. The method of claim 15, wherein the compound is (1S,2S)-2-Phenyl-cyclopropanecarboxylic acid {(S)-1-[6-(oxetan-3-yloxy)-pyridin-3-yl]-ethyl}-amide or a pharmaceutically acceptable salt thereof.

19. The method of claim 15, wherein the compound is (1S,2S)-2-Phenyl-cyclopropanecarboxylic acid ((R)-2-hydroxy-1-{6-[(R)-(tetrahydro-furan-3-yl)oxy]-pyridin-3-yl}-ethyl)-amide or a pharmaceutically acceptable salt thereof.

20. The method of claim 15, wherein the compound is (1S,2S)-N-[(1R)-2-hydroxy-1-[6-[(3S)-tetrahydrofuran-3-yl]oxy-3-pyridyl]ethyl]-2-phenyl-cyclopropanecarboxamide or a pharmaceutically acceptable salt thereof.

21. The method of claim 15, wherein the compound is (1S,2S)-2-Phenyl-cyclopropanecarboxylic acid {(R)-2-hydroxy-1-[6-(tetrahydro-pyran-4-yloxy)-pyridin-3-yl]-ethyl}-amide or a pharmaceutically acceptable salt thereof.

* * * * *